United States Patent [19]

Chiu

[11] Patent Number: 5,319,144

[45] Date of Patent: Jun. 7, 1994

[54] PROCESS FOR PRODUCTIN OF 4,4'-THIOBIS PHENOLS

[75] Inventor: I. Ching Chiu, Houston, Tex.

[73] Assignee: Pennzoil Products Company, Houston, Tex.

[21] Appl. No.: 97,911

[22] Filed: Jul. 28, 1993

Related U.S. Application Data

[63] Continuation of Ser. No. 831,584, Feb. 5, 1992, abandoned.

[51] Int. Cl.$^5$ .................. C07C 319/24; C07C 319/14
[52] U.S. Cl. .......................................... 568/23; 568/48
[58] Field of Search ..................... 568/23, 48

[56] References Cited

U.S. PATENT DOCUMENTS 3,835,196  9/1974  Fujisawa et al. ................. 568/23

Primary Examiner—Marianne M. Cintins
Assistant Examiner—Margaret J. Page
Attorney, Agent, or Firm—Lowe, Price, LeBlanc & Becker

[57] ABSTRACT

Thiobisphenols of the formula:

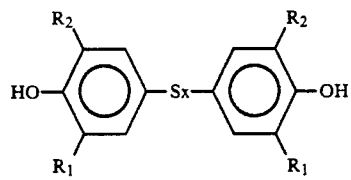

wherein X is 1, 2, 3 or 4 and $R_1$ and $R_2$ are straight or branch-chained alkyl group of 1 to 10 carbon atoms, which are useful as antiodiants and synergists for antioxidants, are prepared by reaction of a 2,6-dialkylphenol with an excess of sulfur in a solvent comprising a mixture of an alcohol and water wherein the solvent contains from 10 to 50 wt. % of water.

8 Claims, No Drawings

PROCESS FOR PRODUCTIN OF 4,4'-THIOBIS PHENOLS

This application is a continuation of application Ser. No. 07/831,584 filed Feb. 5, 1992 now abandoned.

FIELD OF THE INVENTION

This invention relates to a process for the production of 4,4'-thiobis(2,6-dialkyl) phenols by the reaction of 2,6- dialkylphenols with sulfur to produce the desired product in high yields and purity.

BACKGROUND ART 4,4'-thiobis(2,6-dialkyl)phenols are known compounds useful in various areas. For example, 4,4'-thiobis(2,6-di-t-butyl)phenol is a well known antioxidant and an effective synergist for other antioxidants. It is known from U.S. Pat. No. 3,835,196 to prepare compounds of this type by reacting 2,6-di-t butylphenol with an excess of sulfur in a solvent under basic conditions. This patent indicates that the solvent can be any solvent which would not react with the basic materials of the final product. Alcohols such as methanol, ethanol and ethylene glycol as well as solvents such as pyridine, dimethylformamide and dimethyl acetamide are indicated as preferred. Mixtures of these solvents in water in any proportions are indicated for use. In the specific example in this patent, the solvent was a 95% ethanol solution in water.

The present invention provides an improved solvent system for production of desired and preferred products of this type in high yields and high purity.

SUMMARY OF THE INVENTION

It is accordingly one object of the present invention to provide a method for the preparation of thiobisphenols in high yield and good purity.

It is a further object of the invention to provide a method for the preparation of thiobisphenols by the reaction of dialkylphenols and sulfur in a solvent system which maximizes yields and purity.

In satisfaction of the foregoing objects and advantages, there is provided by the present invention a process for the production of thiobisphenols of the formula:

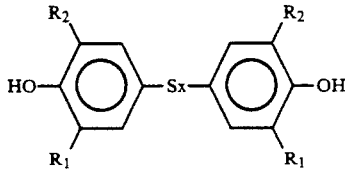

wherein x is 1, 2, 3 or 4 and $R_1$ and $R_2$ are a straight or branch-chained alkyl group of 1-10 carbon atoms, preferably t-butyl which comprises reacting 2,6-dialkylphenol with sulfur in a solvent system comprising a mixture of water and an alcohol of the formula ROH wherein R is alkyl of 1-5 carbon atoms, and wherein said solvent contains at least 10 wt. % water, the reaction being carried out by heating the phenol and sulfur at an elevated temperature, optionally in the presence of a basic reactant, cooling, removing unreacted sulfur and recovering the product in high yield and high purity.

Other objects and advantages of the present invention will become apparent as the description thereof proceeds.

The present invention provides an improved solvent system which maximizes yields and purity of the desired product in the reaction of 2,6-dialkylphenols with sulfur. The following is the general reaction scheme for this synthesis.

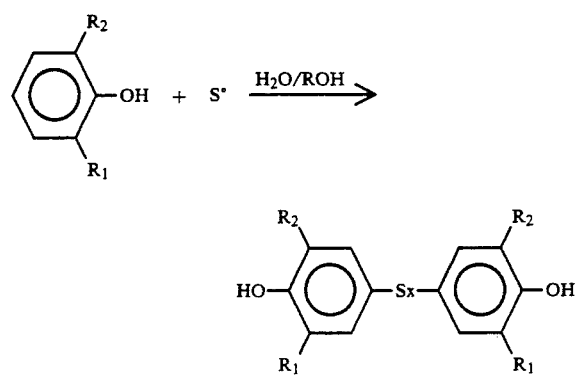

In the above formula $x_1$ $R_1$ and $R_2$ are as defined above.

As indicated above, this general reaction is known from U.S. Pat. No. 3,835,196, wherein 2,6-di-t-butylphenol is reacted with an excess of sulfur in an alcohol solvent under basic conditions. In this patent, the reaction products comprise a mixture of 4,4'-polythiobis(2,6-di-t-butyl)phenols and unreacted or excess sulfur. These products are known for use as antioxidants and as synergists for other antioxidants. It is well known, however, that lubricant oils which contain sulfur have corrosion problems and the polythiobis(2,6-di-t-butyl)phenols produced according to this method may extrude sulfur to corrode metal surfaces contacted by the oils. Therefore, products of this type must be sufficiently pure to pass the ASTM D-1275 copper corrosion test. The method of U.S. Pat. No. 3,835,196 employs column chromatography to separate the unreacted sulfur from the polythio(2,6-di-t-butyl)phenols. However, column chromatography is a very impractical method on a large scale, especially on an industrial scale. Further, the polythiobisphenols are often fractionally recrystallized to isolate each mono, di-, tri-, and tetra-thiobisphenol to try and upgrade the purity of the product to prevent sulfur extrusion in use. It is also reported in the literature that the reductive cleavage of the polysulfide bridge with the Zn/HCl also provides the monothiobisphenol (Fujisawa et al, Synthesis, 1972, Page 38).

The present invention provides an improved process for the production of thiobisphenol in two ways. First, the desired reaction product, i.e., the monothiobisphenol is obtained unexpectedly almost exclusively when the amount of water in the alcoholic solvent is increased in the reaction system to higher than 10 wt. %. Secondly, by making use of the solubility differences between elemental sulfur and the thiobisphenol product in different solvents, the sulfur impurity can be effectively removed. Therefore, according to the improved process of this invention, the final product obtained is a sulfur-free, noncorrosive 4,4'-thiobis(2,6-dialkyl)phenol in good yield and excellent purity.

In conducting this reaction, a dialkyl substituted phenol of the following formula is employed:

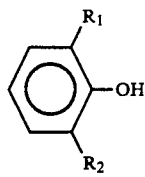

wherein, in the above formula, $R_1$ and $R_2$ are alkyl groups of 1 to 10 carbon atoms but preferably is tertiary-butyl. This phenol s reacted with elemental sulfur, preferably using an excess of the sulfur, e.g, about 2 to 5 mole excess. The reaction is conducted by contacting the reactants in a solvent in the presence of a base usually at a temperature from about 50° C. to the boiling point or reflux point of the solvent for 30 minutes to 5 hours. The basic reactant is preferably an alkali metal hydroxide or alkaline earth metal hydroxide. Sodium hydroxide or potassium hydroxide are preferred. The amount of basic reactant is generally present in about the same amount as the sulfur reactant.

From this reaction, there is obtained a mixture containing unreacted or excess sulfur which is filtered off. The alcohol solvent is then removed by distillation to obtain a crude filtrate containing a trace of sulfur. This product may then be treated with a liquid alkane of up to 10 carbons such as pentane, hexane, heptane or octane, to purify the product. The sulfur contamination remains in the alkane filtrate.

It has been discovered according to this invention that to optimize the yield, an increase of water in the solvent system of greater than 10% and preferably greater than 25% will provide almost exclusively the monothiobisphenol. On the other hand, the reaction yield drops when the aqueous portion of the water exceeds 50%, apparently because the solubility of the 2,6-dialkylphenol becomes poor in the solvent having a high water content.

Accordingly, the main features of the present invention reside in the use of an alcohol water solvent wherein the alcohol can be any alcohol of the formula ROH wherein R contains 1 to 5 carbon atoms including branch chain alkyls. The preferred solvent is an alcohol/water solvent containing from about 10 to 50% of water, or, about 50 to 90% of alcohol. In the second feature of the invention, the crude product recovered from the reaction can be purified to remove excess solvent by heating to the boiling point the crude product in alkane solvents such as pentane, hexane, heptane, or octane normal-hexane. Sulfur is removed with the solvent to permit recovery of the desired product in high yield and good purity.

The following examples are presented to illustrate the invention but it is not to be considered as limited thereto. In the examples and throughout the specification, parts are by weight unless otherwise indicated.

EXAMPLE 1

To optimize the yield, a series of reactions were carried out under the same reaction conditions except that the water content in ethanol was increased. In this reaction 0.2 mole of 2,6-di-t-butylphenol was reacted with the sulfur under the conditions described above. The HPLC analysis of the distribution of the mono-, di-, tri-, and tetra-thiobisphenol in the crude products is shown in Table 1. Unexpectedly, it was discovered that the product favored the monothiobisphenol as the water content was increased in the system. Using 50% aqueous alcohol as solvent, the reaction almost exclusively, gave monothiobisphenol. The reaction yield dropped when the aqueous ethanol exceeded 50%. This is apparently because the solubility of 2,6-di-t-butylphenol becomes bias in the solvent with high water content.

TABLE 1

| % of water in ethanol | Distribution of Polythiobisphenols | | | |
|---|---|---|---|---|
| | R = 1 | R = 2 | R = 3 | R = 4 |
| 5 (US 3,835,196) | 69.9 | 22.6 | 5.4 | 2.1 |
| 10 | 89.0 | 4.4 | 4.8 | 1.5 |
| 25 | 91.7 | 5.9 | 1.6 | 0.8 |
| 50 | 98.0 | 1.3 | 0.5 | 0.1 |

By using the solubility properties of sulfur and thiobisphenols in methanol and hexane, as given in Tables 2 and 3, one can calculate how much solvent is needed to purify the reaction product.

TABLE 2

| | Solubilities of Sulfur | |
|---|---|---|
| Solvent | Temp °C. | mg/ml |
| Hexane | 0 | 1.0 |
| Methanol | 18 | 0.22 |

TABLE 3

| | Solubilities of Thiobisphenols | |
|---|---|---|
| Solvent | Temp °C. | gram/ml |
| Hexane | reflux | 0.90 |
| Methanol | reflux | 0.20 |

For example, when the reaction starts with 0.2 mole of 2,6-di-t-butylphenol, the reaction products should contain, stoichiometrically, 44.2 grams of the monothiobisphenol plus the unreacted (excess) sulfur. Since the solubility of monothiobisphenol in methanol is 0.2 grams/ml at the reflux temperature, 221 ml of methanol are needed to dissolve all the sulfide. After cooling to 18° C., most of the unreacted (excess) sulfur is recrystallized out and filtered off. After stripping off methanol, the filtrate contains crude monothiobisphenol and a trace of sulfur. The obtained crude product when blended in a transformer oil fails the ASTM D-1275 copper corrosion test. The sulfur contamination in the product is estimated to be about 48 mg (0.22 mg/ml×221 ml). The crude product was then refluxed with 48 ml of hexane. After cooling to 0° C., the pure monothiobisphenol is collected. All the sulfur contamination theoretically remains in the hexane filtrate.

EXAMPLE 2

PREPARATION OF 4,4'-THIOBIS (2,6-DI-T-BUTYL)PHENOL

A suspension of 2,6-di-tert-butylphenol (24.36 grams, 0.12 mole), sulfur (11.52 grams), and KOH (87% pure, 11.58 grams) in 60 ml of 50% aqueous ethanol was refluxed for 1 hour. After stripping off ethanol, the reaction was diluted with cold water (100 ml) and then slowly neutralized with 3N HCl (69 ml) at ice-bath temperature. A yellow powder was collected and washed with chilled water. The powder weighed 32 grams after drying. The dried powder was boiled with methanol (133 ml) for 1 hour, followed by gradual cooling to 18° C. The unreacted (excess) sulfur powder was filtered off. After drying, the recovered sulfur weighed 6.2 grams (65% recovered). The filtrate was evaporated to dryness. Hexane (35 ml) was added to the residue and refluxed for 1 hour. The solution was cooled in an ice bath for at least 2 hours. Then, the colorless 4,4'-thiobis (2,6-di-tert-butyl)phenol powder was collected in 70% yield (19 grams). Based on HPLC analysis, the product contains 4,4'-thiobis(2,6-di-t-butyl)phenol and a trace of 4,4'-dithiobis-(2,6-di-t-butyl)phenol. The sulfur contamination in the product was below the detected limit. According to this process, the product passes the ASTM D-1275 copper corrosion test.

The invention has been described herein with reference to certain preferred embodiments; however, as obvious variations thereon will become apparent to those skilled in the art, the invention is not to be considered as limited thereto.

What is claimed is:

1. In a process for the production of substantially sulfur-free thiobisphenols of the formula:

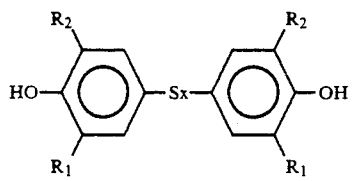

wherein x is 1, 2, 3 or 4 and $R_1$ and $R_2$ are straight or branch-chained alkyl groups of 1-10 carbon atoms, which comprises reacting a 2,6-dialkylphenol with sulfur in a solvent comprising a mixture of water and an alcohol of the formula ROH, wherein R is alkyl of 1 to 5 carbon atoms, the improvement wherein said solvent contains from 10 wt. % to 50 wt. % of water, the reaction is carried out by heating said phenol and said sulfur at a temperature from about 50° C. to the boiling point of the solvent in the presence of a basic reactant, cooling, removing unreacted sulfur, then extracting with a n-alkane and recovering the substantially sulfur-free thiobisphenol product.

2. A process according to claim 1, wherein the phenol reactant is 2,6-di-tertiary-butylphenol.

3. A process according to claim 1, wherein the basis reactant is an alkali metal hydroxide or alkaline earth metal hydroxide.

4. A process according to claim 1, wherein the solvent is a mixture of water and ethanol containing from 10 to 50 wt. % of water.

5. A process according to claim 4, wherein the alkane is n-pentane, n-hexane, n-heptane or n-octane.

6. A process for the production of substantially sulfur-free thiobisphenols of the formula:

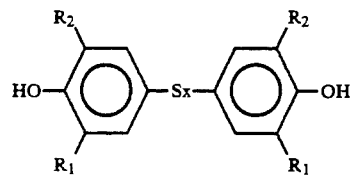

wherein x is 1, 2, 3, or 4, and $R_1$ and $R_2$ are straight or branch chained alkyl groups containing one to 10 carbon atoms, the process comprising reacting a 2,6-dialkylphenol with sulfur in a solvent which comprises a mixture of water and an alcohol of the formula ROH, wherein R is alkyl of 1-5 carbon atoms, and wherein said solvent contains from 10 wt. % to 50 wt. % of water, the reaction being conducted by heating said phenol and said sulfur at a temperature of from 50° C. to the boiling point of the solvent in the presence of an alkali metal hydroxide basic reactant, cooling the reaction mixture, recovering and purifying to remove sulfur contamination by extracting with hot methanol, filtering, then extracting with a liquid alkane containing up to 10 carbon atoms, the sulfur contamination remaining in the alkane extractant, and recovering the substantially sulfur-free thiobisphenol.

7. A process according to claim 6, wherein the solvent is a mixture of ethanol and 10-50 wt. % of water.

8. A process according to claim 6, wherein the alkane extractant is selected from the group consisting of n-pentane, n-hexane, n-heptane and n-octane.

* * * * *

UNITED STATES PATENT AND TRADEMARK OFFICE
CERTIFICATE OF CORRECTION

PATENT NO. : 5,319,144
DATED : June 7, 1994
INVENTOR(S) : I. Ching CHIU

It is certified that error appears in the above-indentified patent and that said Letters Patent is hereby corrected as shown below:

In the Abstract line 4, change "antiodiants" to --antioxidants-- column 1, line 21, change "2,6-di-t butylphenol" to --2,6-di-t-butylphenol-- column 3, line 14, change "phenol s" to --phenol is--

Signed and Sealed this

Tenth Day of January, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,319,144
DATED : June 7, 1994
INVENTOR(S) : I. Ching CHIU

It is certified that error appears in the above-indentified patent and that said Letters Patent is hereby corrected as shown below:

In the Abstract line 4, change "antiodiants" to --antioxidants--.

Column 1, line 21, change "2,6-di-t butylphenol" to --2,6-di-t-butylphenol--.

Column 2, line 26, change "x₁" to --x,--.

Column 3, line 14, change "phenol s" to --phenol is--.

Signed and Sealed this

Second Day of May, 1995

Attest:

BRUCE LEHMAN

Attesting Officer    Commissioner of Patents and Trademarks